United States Patent [19]
Renjilian et al.

[11] Patent Number: 4,891,098
[45] Date of Patent: Jan. 2, 1990

[54] DYNAMIC FILTRATION SIMULATOR

[75] Inventors: Armen Renjilian, Colonie; Francis L. Davenport, Ballston Lake, both of N.Y.

[73] Assignee: Albany International Corp., Menands, N.Y.

[21] Appl. No.: 298,657

[22] Filed: Jan. 18, 1989

[51] Int. Cl.$^4$ ................. G01N 15/00; B01D 37/00
[52] U.S. Cl. ................. 162/198; 73/64.1; 162/263; 210/90; 210/416.1; 210/767
[58] Field of Search .............. 162/198, 263; 210/416.1, 196, 195.1, 90, 767; 73/38, 64.1

[56] References Cited

U.S. PATENT DOCUMENTS

| | | | |
|---|---|---|---|
| 3,478,601 | 11/1969 | Niebergall | 73/38 |
| 3,872,710 | 3/1975 | Louvel | 73/61.4 |
| 3,946,596 | 3/1976 | Shiuh | 162/198 |
| 4,583,396 | 4/1986 | Hunt et al. | 73/61 R |
| 4,662,911 | 5/1987 | Karna et al. | 162/198 |

*Primary Examiner*—Karen M. Hastings
*Attorney, Agent, or Firm*—Kane, Dalsimer, Sullivan, Kurucz, Levy, Eisele & Richard

[57] ABSTRACT

This invention is directed to a filtration simulator. More specifically, this invention is directed to a Dynamic Filtration Simulator (DFS) and method of determining the interaction and effect on liquid flow of additives to paper stock in a papermaking machine, which comprises:

(a) admixing one or more additives to be tested with paper stock in a slurry tank to form an aqueous paper stock slurry;

(b) pumping said slurry from step (a) to a filtration means comprising permeable filter material, the interior of said filtration means being in fluid communication with an exit pipe which is in fluid communication with said slurry tank, whereby aqueous slurry permeates said filter material to form a permeate and said permeate flows through said exit pipe back to said slurry tank;

(c) measuring the pressure and volume flow of the aqueous paper stock slurry into the filtration means; and (d) measuring the pressure and volume flow of the aqueous permeate.

18 Claims, 6 Drawing Sheets

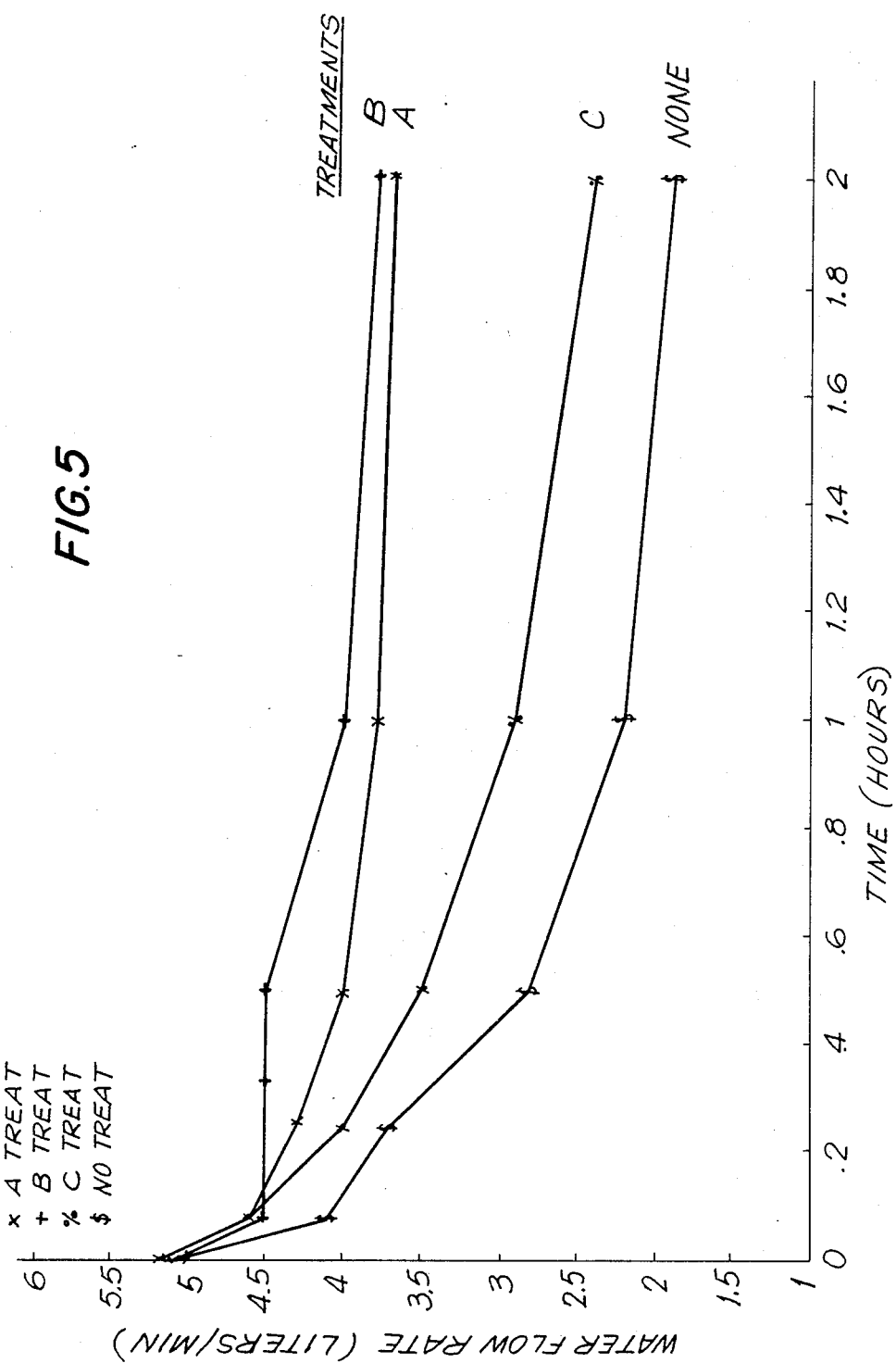

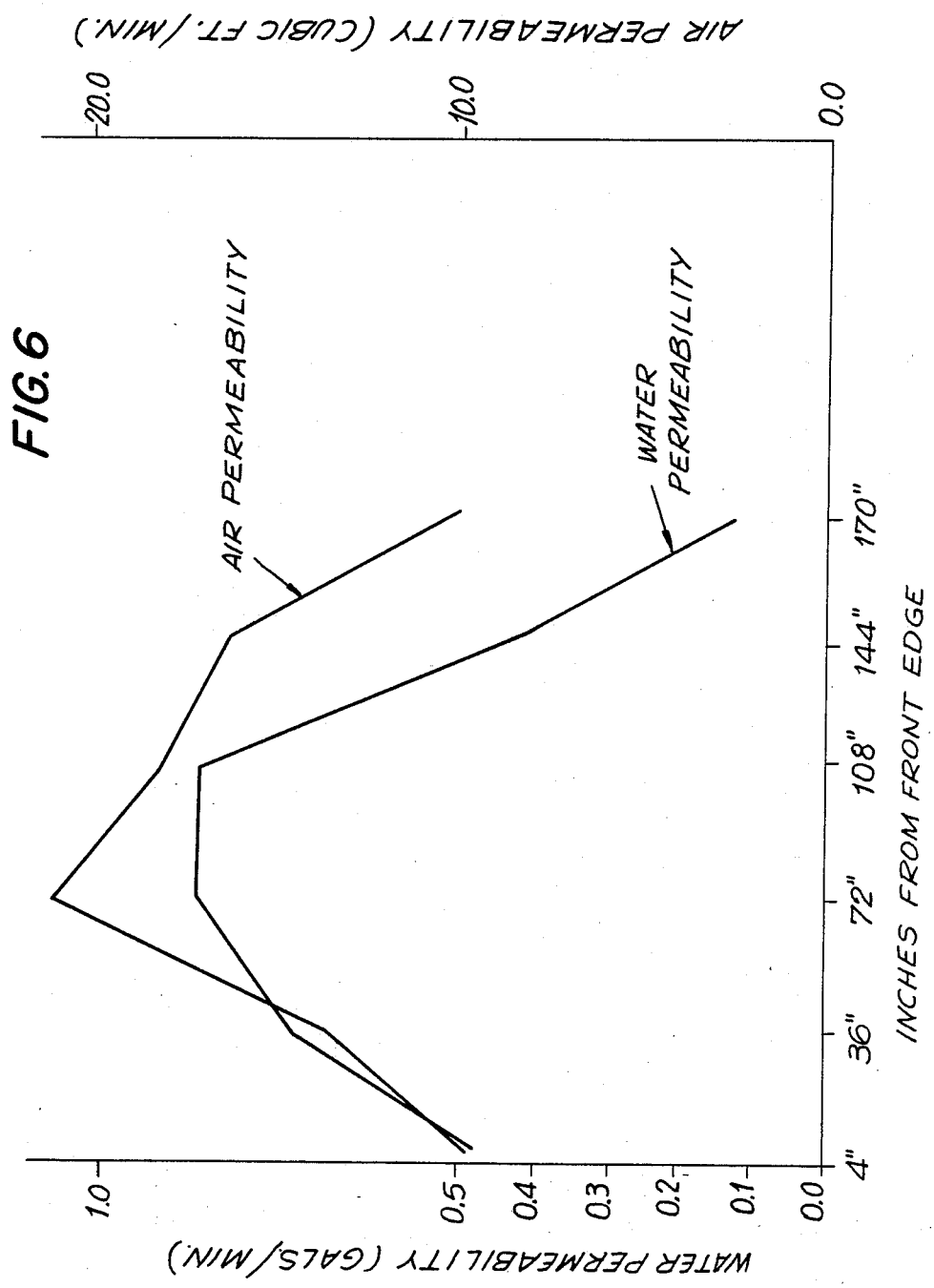

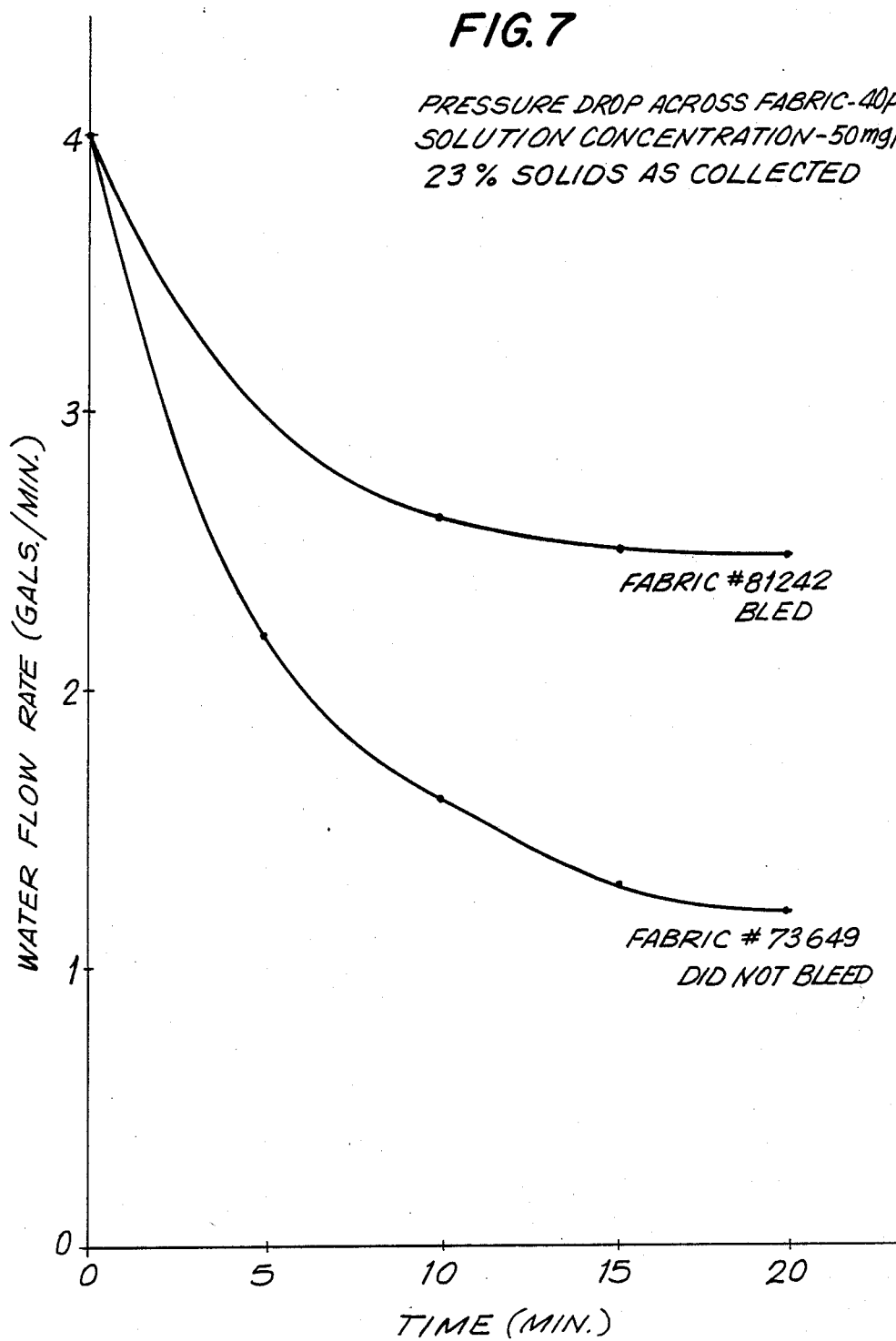

DYNAMIC FILTRATION SIMULATOR

FIELD OF THE INVENTION

This invention is directed to a filtration simulator. More specifically, this invention is directed to a dynamic filtration simulator useful to determine the effects of additives to paper.

BACKGROUND OF THE INVENTION

In recent years there has been a rapid increase in the use of various additives in recipes for papermaking. The chemicals used as additives interact with wood fibers and other added materials such as paper fines, starches, clays, carbonates, alum, and natural resins. As a result of this interaction, retention of fine particles to the fibrous sheet of paper is enhanced, and the properties of paper, such as wet or dry strength or printability, are improved.

Many of these additives are polyelectrolytes and possess anionic and cationic charges which vary as a function of pH and the use of other electrolytes in the papermaking system. Also, some chemicals are intended to change the particle size of fines, causing them to flocculate into larger aggregates.

In many instances a paper mill experiments with the use of such additives not in a pilot plant but on a production papermaking machine. Such experimentation is at great expense since malfunctioning caused by such very active additives can result in excessive machine downtime due to undesirable chemical residue and in build-up on papermaking machine surfaces and press fabrics.

Thus, experimentation involving such new additives or new procedures, as well as adjustments of other process parameters such as pH and concentration, are not advantageously carried out on a production papermaking machine. There is a need to develop another method of testing wherein the expense associated with testing on a production papermaking machine can be avoided.

OBJECTS OF THE INVENTION

It is an object of the invention to provide a filtration simulator.

It is another object of the invention to provide a dynamic filtration simulator (DFS) for testing additives to paper recipes.

It is a further object of the invention to provide a method for study of the ability of press fabrics to remove water from paper stocks formulated with different chemicals and under different conditions.

It is a yet further object of the invention to provide a method and apparatus for testing the effects of additives to paper stock in a paper machine, which comprises:

(a) admixing one or more additives to be tested with paper stock in a slurry tank to form an aqueous paper stock slurry;

(b) pumping said slurry from step (a) to a filtration means comprising permeable filter material, the interior of said filtration means being in fluid communication with an exit pipe which is in fluid communication with said slurry tank, whereby aqueous slurry permeates said filter material to form a permeate and said permeate flows through said exit pipe back to said slurry tank;

(c) measuring the pressure and volume flow of the aqueous paper stock slurry prior to entry into the filtration means; and (d) measuring the pressure and volume flow of the permeate as it flows from the filtration means.

These and other objects of the invention will become more apparent in the discussion below.

BRIEF DESCRIPTION OF THE DRAWINGS

FIGS. 4 to 7 each represent a graph of certain test results.

DETAILED DESCRIPTION OF THE INVENTION

Figure 1:
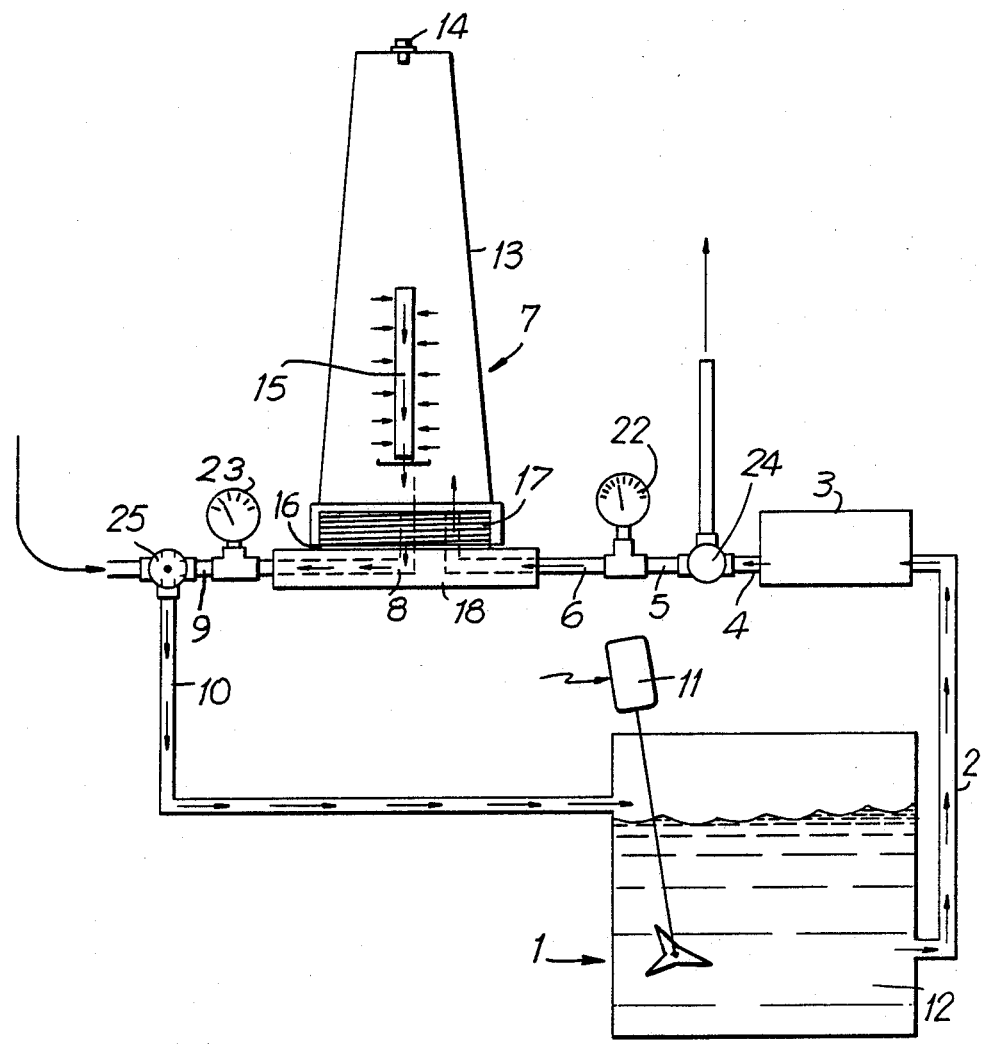
FIG. 1 represents a plan view of an embodiment of the invention.

Applicants have discovered a way of operating on a small scale to study the effects of various additives and conditions upon paper stocks. According to the invention, one or more additives to be tested with paper stock are admixed in a slurry tank to form an aqueous paper stock slurry, and said slurry is pumped to a sealed vessel having filter means. The filter means comprises a permeable filter material, and the interior of said filter means is in fluid communication with an exit pipe from said sealed vessel, which exit pipe is in fluid communication with said slurry tank. The aqueous slurry permeates said filter material, and the resulting permeate flows through said exit pipe back to the slurry tank. The pressure and volume flow of the aqueous paper stock slurry into the filtration means and the pressure and/or volume flow of the aqueous slurry and permeate, respectively, are measured.

In one preferred embodiment, a papermakers' press fabric is cut to size and made into a filter medium. This is done by gluing or taping the ends of the cut piece onto a form, advantageously cylindrical, to form a tube. This tube is then inserted into a filter cartridge core to form a filter, the filter core preferably being closed on one end. In another preferred embodiment, a piece of press fabric is arranged normal to the flow of water in a holding means having a variable orifice.

A slurry tank is preferably used to make various recipes for paper stock and to adjust pH conditions for experimentation to measure press fabric fluid permeability and system compatibility. Usually a sufficient amount of cellulose fiber is allowed into the system to form a sheet of paper on the press fabric surface. The remainder of the system is stock water containing desired additives and particle fines normally used in the paper mill system to be studied.

This stock water containing paper fines and other chemical and particle components is then pumped into the filter cartridge chamber and allowed to permeate the press fabric filter.

The rate of flow of stock water and the differential pressure on either side of the press fabric are measured as a function of time. Any interaction of stock particles with the press fabric is immediately measurable since both the flow rate and the pressure drop across the press fabric sample are measurable.

Consistent with the invention, the press fabric filter may be comprised of many different design styles and may contain a permanent chemical treatment as a standard. Also, the press fabric may be pre-compacted or may be a sample from a used press fabric returned from a paper mill for testing and evaluation. The particular press fabric material to be used herein can be any press fabric currently used in a papermaking process or a fabric or treatment under development and is not otherwise critical to the invention. The composition and requirements of useful press fabrics are well known to those skilled in the art. A thorough description of useful press fabrics is set forth, for example, in *Paper Machine Felts and Fabrics*, Albany International Corp., 1976, which is incorporated herein by reference.

It is within the scope of the invention that the filter material to be tested could also comprise forming fabric useful in a papermaking machine or another textile assembly or fabric. Forming fabrics are well known to those skilled in the art and are described in references such as the above-mentioned Albany International Corp. publication. A suitable textile assembly of fabric would include any woven or non-woven material that is sufficiently permeable to function in the apparatuses described and with additives to be tested for a particular application. The filter material and additives to be tested need not be limited to the field of papermaking.

One aspect of the invention is directed to a method of testing the effects of additives on liquid flow through a permeable substrate. For example, to test the effects of additives to paper stocks, the method would comprise the steps of:

(a) admixing one or more additives to be tested with paper stock in a slurry tank to form an aqueous paper stock slurry (b) pumping said slurry from step (a) to a filtration means comprising permeable filter material, the interior of said filtration means being in fluid communication with an exit pipe which is in fluid communication with said slurry tank, whereby aqueous slurry permeates said filter material to form a permeate and said permeate flows through said exit pipe back to said slurry tank;

(c) measuring the pressure and volume flow of the aqueous paper stock slurry prior to entry into the filtration means; and (d) measuring the pressure and volume flow of the permeate as it flows from the filtration means.

The invention herein can perhaps be better understood by making reference to the drawings. The arrangement set forth in FIG. 1 comprises a slurry tank 1 in fluid communication through pipe 2 with pump 3, which is in fluid communication through pipes 4, 5, and 6 with filtration means 7. Water exits filtration means 7 through pipe 8 and returns to slurry tank 1 through pipes 9 and 10. Slurry tank 1 has mixer 11, or comparable mixing or stirring means, to provide a homogeneous mixture of stock water 12 to be pumped through the system.

Filtration means 7 comprises a receiving vessel 13 having a vent 14 and felt holding member 15, which is in fluid communication with pipe 8. The bottom or open end 16 of receiving vessel 13 is secured in releasable fashion, such as with clamps or by reciprocal screw threads 17, to base 18.

A piece of press fabric is formed into fabric member 19, which is slipped onto a portion 20, preferably cylindrical, of fabric holding member 15. The upper end 21 of fabric holding member 15 is closed and may optionally comprise means for holding fabric member 19 in place.

The differential pressure across fabric member 19 is measured by pressure gauges 22 and 23. At similar locations other instrumentation (not shown) could measure volume flow. Also, the system can be purged or cleansed by use of backflush valves 24 and 25.

Figure 3:
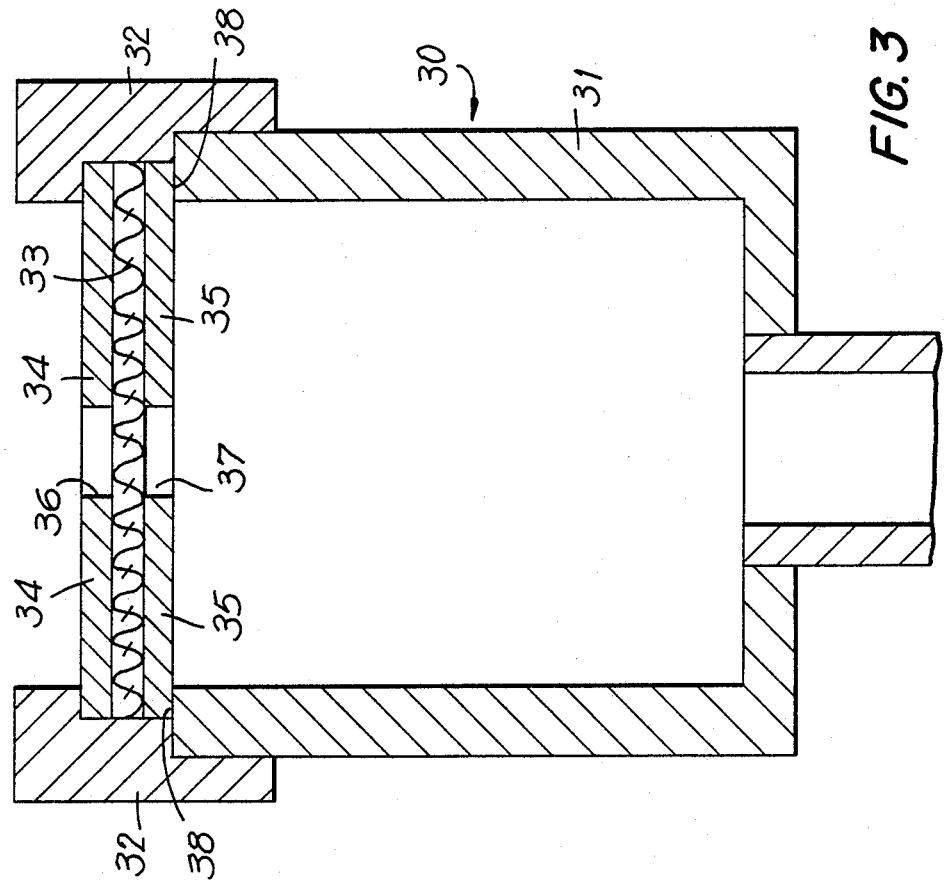
FIG. 3 represents a cross-sectional view of a filtration means according to the invention.
Figure 2:
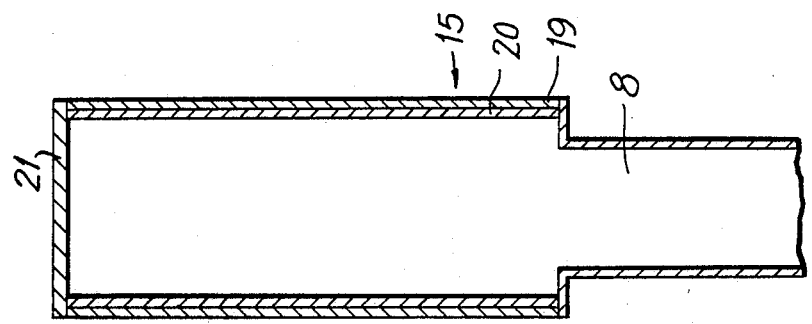
FIG. 2 represents a cross-sectional view of a filter material holding member according to the invention.

In FIG. 3 the filtration means 30 comprises vessel 31 having holding means 32, which is releasably attached, for example, by clamps or screw threads (not shown), to vessel 31. A press fabric sample 33 is positioned between plates 34 and 35, which have orifices 36 and 37, respectively. The orifices 36 and 37, which preferably are circular and from about 1/10 to ½ in. in diameter, more preferably from about 7/64 to 11/64 in. in diameter, must be aligned. Plates 34 and 35 are held tight against fabric sample 33 and the downstream edge 38 of vessel 31 by securing means 32. Plates 34 and 35 are preferably at least 0.2 in. thick, more preferably from about 0.25 to 0.75 in. thick.

It would be appreciated by those skilled in the art that the parts of the apparatus of the invention can be made from conventional materials. For example, pipes 2, 4, 5, 6, 8, 9, and 10 can be metal or PVC, and tank 1 and vessels 7 and 30 could be metal, plastic, or glass, metal or glass being preferred.

The dynamic filtration simulator device and procedure disclosed herein are both simple and versatile. More specifically, the procedure and device are sufficiently versatile to measure various paper mill additives and changes in flow characteristics resulting from such additives and stock conditions.

The following examples are intended to illustrate the invention and should not be construed as limiting it thereto.

EXAMPLES

EXAMPLE 1

An apparatus having the configuration shown in FIG. 1 was assembled. A piece of DURAGROOVE ® press fabric (available from Albany International Corp., Felt Div.) having the dimensions 6"×3" was formed into a cylindrical filter of the dimensions 6" in length, 1¼" o.d., and ⅞" i.d. and placed upon a cylindrical support. Aqueous solution was circulated from a mixing tank, through the filter, and back to the mixing tank. The volume of the fluid circulated was measured by a flowmeter device downstream of the filter and before return to the mixing tank. The following tests were conducted to answer process questions. Tables I and II below show fabric flow rate changes with different sequences of adding alkali, alum, and rosin to a paper mill stock system.

The additives added to the aqueous solution and the flow rate measurements are set forth in the following table:

TABLE I

|  | Time (min.) | Flow Rate (liters/min.) |
|---|---|---|
| Initial flow rate (water only) | 0.0 | 5.3 |
| Addition of sufficient NaOH and alum (0.3% soln) to raise pH to 9.0 | 15.0 | 4.8 |
| Addition of rosin (1% soln) | 16.0 | 4.6 |
|  | 16.5 | 3.8 |
|  | 17.5 | 3.8 |
| Addition of sufficient $H_2SO_4$ to lower pH to 5.5 | 18.5 | 3.0 |

TABLE I-continued

| | Time (min.) | Flow Rate (liters/min.) |
|---|---|---|
| Final measurement at pH 5.5 | 37.5 | 0.8 |

EXAMPLE 2

In a set-up similar to that described in Example 1, the additives were added in a different order:

TABLE II

| | Time (min.) | Flow Rate (liters/min.) |
|---|---|---|
| Initial flow rate (water only) | 0.0 | 5.3 |
| Addition of NaOH and rosin (0.3% soln) to raise pH of solution to 9.0 | 1.0 | 3.8 |
| Addition of $H_2SO_4$ (1% soln) to lower pH to 5.5 | 21.0 | 4.8 |
| Addition of alum | 22.0 | 3.4 |
| Final measurement at pH 5.5 | 27.0 | 0.9 |

The above results indicate that the addition of additives, especially alum, results in a deposit which reduces the permeability of the press fabric. The process must be closely monitored to ensure that alum is used in a sequence to maximize its benefit to paper properties without affecting the functioning of the fabric to remove water.

EXAMPLE 3

An apparatus having the configuration shown in FIG. 3 was assembled. A piece of DURAGROOVE® press fabric having a diameter of 5.0 cm was placed across the apparatus opening. Three separate press fabrics were used. One press fabric was untreated, and the other two press fabrics were treated with a hydrophilic Treatment A and with a hydrophobic Treatment B, respectively.

Figure 4:
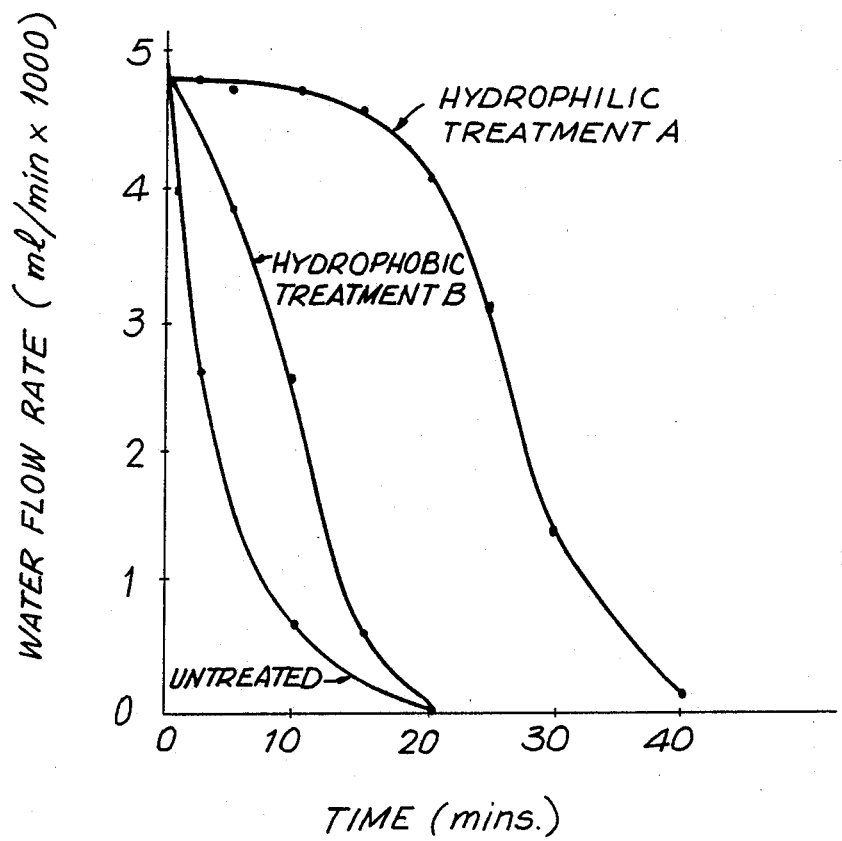

A 1% solution of potassium rosinate was prepared in the slurry tank, and this solution flowed through the treated and untreated press fabrics. The results are shown in FIG. 4.

These results show that regardless of the treatment all press fabrics will eventually fill up with rosin size unless they are kept clean through conditioning equipment. However, in this example the hydrophilic treated press fabric took considerably longer to fill up than the untreated and hydrophobic treated press fabrics. The hydrophobic treated press fabric (B) tested better than the untreated press fabric. The reason for this is not known.

EXAMPLE 4

With use of the apparatus and treatments described in Example 3, tray water from a paper mill site was circulated through test press fabrics (available from Albany International Corp., Felt Div.). The results are set forth in FIG. 5. Obviously, press fabric with Treatment B maintained higher flow rate properties than the others. This Treatment B press fabric was run on the production paper machine and ran with lower vacuum levels at the suction box than other fabrics run.

EXAMPLE 5

A used DURAGROOVE® press fabric was analyzed for filling with a resinous material by use of an apparatus such as is described in Example 3. It was found that the front edge was less filled with this resin than from the center to the back edge. Additionally, the press fabric exhibited a wear streak approximately 72 inches from the front edge. The air permeability profile using a modified Frazier permeability tester was compared with a water flow profile obtained with the DFS equipment. Air permeabilities are performed on press fabrics returned dry. The present wet procedure of the invention shows a greater edge-to-edge variation. This deviation was shown to result from a hydrophilic polymer resin which while wet, swells to greater volume, thus using more press fabric void volume than when dry. Results obtained are shown in FIG. 6.

EXAMPLE 6

The causes of press fabric bleeding, a term used to describe the paper fines and fillers that pass through a press fabric, are numerous and may be press fabric or paper stock related. As described below, both aspects were involved:

A problem mill was experimenting simultaneously with increasing the clay filler from 90 to 200 lbs. per ton and at the same time changing the retention aid to a higher charge and higher molecular weight product; however, a lesser amount was used than was used previously. In addition, the mill was using about 8 lbs. of rosin size/ton of paper with 16 lbs. per ton of alum. These quantities were not changed. Press fabrics supplied prior to these changes did not cause bleeding. However, after the change in the additives, all press fabrics from all suppliers began to bleed.

Samples of bled material were collected from the pickup position stretch roll. The dried solids were 63% clay and 37% cut paper fibers. No alum or retention aid was present in this material, indicating that there was not enough retention agent for all the particles present. The collected material was redispersed in the slurry tank of the filtration apparatus at a concentration of 50 mg per liter, 23% solids as collected, and tested using the equipment in FIG. 3, with press fabrics Nos. 73649 and 81242, which varied in density. During testing the pressure differential ($\Delta P$) across the press fabric samples ranged from 6.5 psi at the start to 40 psi at the end. These press fabrics were eventually run on the production papermaking machine. The results predicted by use of the DFS apparatus (see, FIG. 7) show the press fabric with the lower flow resistance and lower density, No. 81242, to cause bleeding on the papermaking machine.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A method to determine the interaction and effect on liquid flow of additives to paper stock in a papermaking machine, which comprises:
   (a) admixing one or more additives to be tested with paper stock in a slurry tank to form an aqueous paper stock slurry;
   (b) pumping said slurry from step (a) to a filtration means having an interior space and comprising permeable filter material, the interior space of said filtration means being in fluid communication with an exit pipe which is in fluid communication with said slurry tank, whereby aqueous slurry permeates said filter material to form a permeate and said permeate flows through said exit pipe back to said slurry tank;

(c) measuring the pressure and volume flow of the aqueous paper stock slurry into the filtration means; and (d) measuring the pressure and volume flow of the aqueous paper stock permeate.

2. The method of claim 1, wherein the permeable filter material is in cylindrical form and is positioned on a cylindrical holding means.

3. The method of claim 1, wherein the permeable filter material is positioned across an opening into said interior space.

4. The method of claim 1, wherein the permeable filter material is a papermaker's press fabric or forming fabric.

5. The method of claim 4, wherein the permeable filter material is a papermaker's press fabric.

6. A method to determine the interaction and effect of additives on liquid flow through a permeable substrate, which comprises:

(a) admixing one or more additives to be tested with an aqueous base liquid in a slurry tank to form an aqueous slurry;

(b) pumping said slurry from step (a) to a filtration means having an interior space and comprising permeable filter material, the interior space of said filtration means being in fluid communication with an exit pipe which is in fluid communication with said slurry tank, whereby aqueous slurry permeates said filter material to form an aqueous permeate and said aqueous permeate flows through said exit pipe back to said slurry tank;

(c) measuring the pressure and volume flow of the aqueous slurry into the filtration means; and (d) measuring the pressure and volume flow of the aqueous permeate.

7. The method of claim 6, wherein the permeable filter material is in cylindrical form and is positioned on a cylindrical holding means.

8. The method of claim 6, wherein the permeable filter material is positioned across an opening into said interior space.

9. The method of claim 6, wherein the permeable substrate is a woven or non-woven textile assembly or fabric.

10. An apparatus for testing the effect of additives to paper stock in a papermaking machine, which comprises:

a slurry tank containing one or more additives to be tested with paper stock and forming an aqueous paper stock slurry, said slurry tank having inlet and outlet pipes, and means for admixing said additive or additive with said paper stock;

filtration means comprising permeable filter material and having an interior space, an exit pipe, and an inlet pipe, said inlet pipe being in fluid communication with the outlet pipe of the slurry tank to convey aqueous paper stock slurry to an outer surface of the permeable filter material, said interior space being in fluid communication with said outlet pipe, and said outlet pipe being in fluid communication with the inlet pipe of the slurry tank to convey aqueous stock permeate to the slurry tank;

means to measure the pressure and volume flow of the aqueous paper stock slurry into the filtration means; and means to measure the pressure and volume flow of the aqueous paper stock permeate.

11. The apparatus of claim 10, wherein the permeable filter material is in cylindrical form and is positioned on a cylindrical holding means.

12. The apparatus of claim 10, wherein the permeable filter material is positioned across an opening into said interior space.

13. The apparatus of claim 10, wherein the permeable filter material is a papermaker's press fabric or forming fabric.

14. The apparatus of claim 13, wherein the permeable filter material is a papermaker's press fabric.

15. An apparatus for testing the effect of additives on liquid flow through a permeable substrate, which comprises:

a slurry tank containing one or more additives to be tested with an aqueous base liquid and forming an aqueous slurry, said slurry tank having inlet and outlet pipes, and means for admixing said additive or additives with said aqueous base liquid;

filtration means comprising permeable filter material and having an interior space, an exit pipe, and an inlet pipe, said inlet pipe being in fluid communication with the outlet pipe of the slurry tank to convey aqueous slurry to an outer surface of the permeable filter material, said interior space being in fluid communication with said outlet pipe, and said outlet pipe being in fluid communication with the inlet pipe of the slurry tank to convey aqueous permeate to the slurry tank;

means to measure the pressure and volume flow of the aqueous slurry into the filtration means; and means to measure the pressure and volume flow of the aqueous permeate.

16. The apparatus of claim 15, wherein the permeable filter material is in cylindrical form and is positioned on a cylindrical holding means 17. The apparatus of claim 15, wherein the permeable filter material is positioned across an opening into said interior space.

18. The apparatus of claim 15, wherein the permeable substrate is a woven or non-woven textile assembly or fabric.

* * * * *